United States Patent [19]

Meers

[11] 4,059,489
[45] Nov. 22, 1977

[54] PRODUCTION OF GLUCOSE ISOMERASE

[75] Inventor: John Laurence Meers, Stockton-on-Tees, England

[73] Assignee: Imperial Chemical Industries Limited, London, England

[21] Appl. No.: 595,316

[22] Filed: July 11, 1975

[30] Foreign Application Priority Data

July 30, 1974  United Kingdom ............... 33578/74
Dec. 30, 1974  United Kingdom ............... 55994/74

[51] Int. Cl.² ...................... C12D 13/02; C12D 13/10
[52] U.S. Cl. .................................. 195/31 F; 195/65; 195/115
[58] Field of Search .............. 195/65, 66 R, 115, 31 F

[56] References Cited

U.S. PATENT DOCUMENTS 2,822,319  2/1958  Monod ................................. 195/115
3,396,083  8/1968  Callow ............................. 195/115 X

OTHER PUBLICATIONS

Tempest et al., Journal of General Microbiology, vol. 41, pp. 143-150 (1965).
Maclennan et al., Journal of General Microbiology, vol. 45, pp. 289-302 (1966).
Takasaki, Agricultural and Biological Chemistry, vol. 30, No. 12, pp. 1247-1253, (1966).

Primary Examiner—Lionel M. Shapiro
Attorney, Agent, or Firm—Cushman, Darby & Cushman

[57] ABSTRACT

A process for the continuous production of glucose isomerase by maintaining a nutrient in the culture medium at a concentration which is limiting to growth. Preferably the growth limiting nutrient is the carbon source. The invention also covers a process for isomerizing glucose to fructose using continuously prepared glucose isomerase. Important conditions for culturing the glucose isomerase producing microorganism are the dissolved oxygen tension and dilution rate.

15 Claims, No Drawings

PRODUCTION OF GLUCOSE ISOMERASE

This invention relates to the production of glucose isomerase and to the enzymatic conversion of glucose to fructose.

In recent years a considerable amount of research has been directed towards the development of processes for the conversion of glucose to fructose since fructose is considerably sweeter. The most suitable processes are those in which the conversion is brought about by the enzyme glucose isomerase. Thus considerable attention has been paid to methods for producing this enzyme. Up to the present the methods suggested for the production of the enzyme have been batch methods.

We have now found that when glucose isomerase is produced by continuous fermentation using suitable conditions, the yield of enzyme (both in terms of the amount of enzyme produced per gm of carbon source and in terms of enzyme production per unit of fermenter volume) and its activity in the isomerization of glucose to fructose can be improved.

According to the present invention we provide a process for producing glucose isomerase enzyme or an enzyme preparation containing glucose isomerase by continuously cultivating a glucose isomerase-producing microorganism in a culture medium comprising a source of assimilable carbon and inorganic nutrients under conditions suitable for production of said enzyme or enzyme preparation and continuously recovering said enzyme or enzyme preparation wherein the concentration of a nutrient source, especially the carbon source, in the culture medium is maintained at a level such as to be limiting to growth.

Further according to the present invention we provide a process for isomerizing glucose to fructose using a glucose isomerase enzyme or an enzyme preparation containing glucose isomerase which has been produced by continuously cultivating a glucose isomerase-producing microorganism in a culture medium comprising a source of assimilable carbon and inorganic nutrients under conditions suitable for production of said enzyme or enzyme preparation and continuously recovering said enzyme or enzyme preparation wherein the concentration of a nutrient source, especially the carbon source, in the culture medium is maintained at a level such as to be limiting to growth.

In the specification the nutrient source whose concentration is maintained at a level such as to be limiting to growth is referred to as the limiting nutrient.

The process of the invention for the production of glucose isomerase is commenced by culturing a microorganism by a conventional batch method. When the culture is growing satisfactorily continuous addition of nutrients is commenced, culture being removed from the fermenter at a similar rate to that at which nutrients are added. Suitable nutrients are sources of carbon, nitrogen, phosphorus, magnesium, sulphur, potassium and trace elements. Frequently a source of organic nitrogen which may contain growth factors, e.g. yeast extract or corn steep liquor is also included. The nutrients are preferably added to the culture in concentrations (% w/w of the source compound) within the ranges (precentages are by weight):

Carbon source — 0.05 – 10%
Nitrogen source — 0.001 – 3%
Phosphorus source — 0.01 – 0.5%
Magnesium source — 0.001 – 0.2%
Sulphur source — 0.01 – 0.25%
Potassium source — 0.01 – 0.25%
Organic nitrogen source — 0.01 – 5%
Trace elements — in excess In the process of this invention for producing glucose isomerase, the limiting nutrient, e.g. the carbon source, is present in concentrations such that further increase in the dry weight of the microorganisms used is limited only by lack of further quantities of the limiting nutrient.

Any glucose isomerase-producing microorganism may be used in the process of the invention for producing the enzyme or enzyme preparation. Suitable microorganisms include strains of the genera Streptomyces, Arthrobacter, Mycobacterium and Curtobacterium. The last genus comprises strains previously classified into the genera Brevibacterium and Corynebacterium and is defined by K Yamada and K Komagata in J Gen Appl Microbiol, 18, 417–431, (1972) at pp 424–5. The use of strains of the genus Curtobacterium is described in our co-pending UK Application No. 13994/74.

Examples of suitable Curtobacterium strains for use in the process of the invention are glucose isomerase producing strains of *Curtobacterium citreum* — e.g. NCIB 10702, *Curtobacterium pusillum* — e.g. NCIB 10354, *Curtobacterium luteum* — e.g. NCIB 11029, *Curtobacterium helvolum* — e.g. NCIB 10352 & 10353 and *Curtobacterium alvedum* — e.g. NCIB 11030, all of which were previously classified into the genus Brevibacterium. Also useful are Curtobacterium strains GS/4 and LW/3 whose characteristics are described in our co-pending UK Application No. 13994/74 (corresponding to New Zealand Patent Application No. 177026, South African Patent Application No. 1898/75 and U.S. Ser. No. 561,662) and cultures of which have been deposited with the following Culture Collections and have been given the following Accession Nos.:

1. The National Collection of Industrial Bacteria (NCIB), Torry Research Station, Aberdeen, Scotland, UK — NCIB Accession Nos. NCIB 11072 & 11073 respectively.
2. U.S. Department of Agriculture, Agricultural Research Service, Northern Regional Research Laboratory (NRRL), Peoria, Illinois — NRRL Accession Nos. NRRL B-8069 and B-8068 respectively.
3. The Fermentation Research Institute (FRI), Japan — FRI Accession Nos. FERM 2975 & 2974 respectively.

Examples of very useful strains of other genera are Arthrobacter nov. sp. strains NRRL B 3724, 3725, 3726, 3727 and 3728, *Streptomyces albus* strain YT-No.4 and *Mycobacterium smegmatis* strain ATCC 19420.

In the method for producing glucose isomerase or an enzyme preparation containing glucose isomerase, the glucose isomerase producing microorganism is first grown in a batch culture before being transferred to continuous cultivation. For example an inoculum containing a glucose isomerase producing strain is prepared, e.g. on an agar slant, and is used to inoculate a suitable culture medium. There the organism is grown in batch culture, preferably for 4 to 48 hrs. An aliquot or the entire culture is then used to inoculate a larger volume of nutrient. This may be repeated one or more times before continuous cultivation is commenced. Microbial cells containing the enzyme may be separated from the culture medium which is continuously withdrawn from the enzyme production process by any known means. Preferably the whole cells are used to carry out the isomerization of glucose to fructose. However, if desired the enzyme may be extracted from the cells by any suitable method or the final culture itself may be used without separating the cells, in the conversion of glucose to fructose. Using the final culture itself in this way enables the glucose to fructose isomerization to be carried out on a continuous basis, the culture proceeding continuously from the isomerase production process to the isomerization process.

The culture medium for the production of the enzyme or enzyme preparation preferably contains as the carbon source a suitable carbohydrate e.g. glucose and/or xylose, a suitable organic acid or salt thereof, e.g. an acetate, or an alcohol such as ethanol. It may also contain complex organic nutrients such as a vitamin rich broth comprising yeast extract, meat extract, corn steep liquor etc. The nitrogen source is suitably ammonia, an ammonium salt, a nitrate, an amino acid or urea and the phosphorus source suitably a phosphate. Other elements present preferably include magnesium, potassium and sulphur, e.g. added as magnesium sulphate and potassium sulphate and trace elements such as iron, cobalt, zinc, copper, manganese, calcium etc. The preferred proportions in which the various nutrients are present in the culture medium for production of the enzyme will vary to some extent depending upon the microorganism employed and other factors. Suitable proportions in any particular instance may be determined readily by a competant microbiologist.

During production of glucose isomerase the culture medium is preferably maintained at a temperature within the range 20° to 55° C, the precise temperature depending upon the organism used. In the case of an Arthrobacter strain the temperature is suitably within the range 25° to 37° C, the range 25° to 33° C being preferred and the range 28° to 32° C being especially suitable. Preferably the pH of the medium is maintained within the range 4.5 to 8.5, especially 6.0 to 8.0, again depending on the organism used.

Suitably the dissolved oxygen tension in the medium is controlled within the range 0 - 150 mms of mercury, the range 1 - 100 mms of mercury being preferred and the range 30 to 100 mms of mercury being especially suitable.

The term dissolved oxygen tension (DOT) means the partial pressure of oxygen in the liquid — see the article by Maclennan and Pirt, J. Gen Microbiol. (1966), 45, 286–302, in particular page 290. The dilution rate is preferably within the range 0.05 - 0.4 hrs$^{-1}$ The dilution rate D is the rate of exchange of medium in the fermenter and is given by the ratio of flow rate F to the total medium volume V in the fermenter ie D = (F)/(V) and has dimensions of hrs$^{-1}$.

In the isomerization of glucose to fructose by the method of the invention the temperature is preferably maintained within the range 20° to 90° C, especially 50° to 75° C. The pH of the glucose-containing liquor undergoing isomerization is preferably maintained within the range 5 to 9, particularly 7 to 8.5, if necessary using a suitable buffer system e.g. a phosphate buffer. However, buffering is to be avoided if possible in a large scale process. Other activators such as magnesium, cobalt or manganese ions may be present. Enzyme acitvity may be increased to a maximum by the use of an enzyme cofactor, e.g. cobalt ions added in the form of a cobalt salt such as cobalt chloride. Very suitably the enzyme or enzyme preparation may be immobilised, for example as described in British Specification No. 1,368,650 in the process of which flocculated whole microbial cells containing the enzyme are employed, and used as part of a continuous column process.

The glucose itself may be present in the liquor in amounts up to about 70%, preferably 20 to 50%. It may be included in the liquor as glucose or as a glucose-syrup containing other sugars, e.g. maltose, maltotriose and dextrins.

The glucose isomerase or the enzyme preparation containing it may be included in the liquor in amounts between 4 and 20 GIU (glucose isomerase units) per gram of glucose in the solution. When increasing amounts of enzyme up to several thousand GIU per gram of glucose are added the rate of the isomerization reaction increases.

Preferably the enzyme or the enzyme preparation is immobilised in a fixed bed through which the glucose-containing liquor may be percolated and converted into isomerised syrup.

The glucose isomerase of the present invention may be assayed for its fructose-producing activity by the following assay method:

GLUCOSE ISOMERASE — ASSAY METHOD

An assay of the activity of glucose isomerizing enzyme was performed in the following reaction mixture:

0.2 M phosphate buffer (pH 7.5) — 0.5 ml
2 M glucose — 0.5 ml
0.1 M MgSO$_4$.7H$_2$O — 0.1 ml
0.2 M CoCl$_2$ — 0.1 ml
Enzyme solution — 0.3 ml The solution was made up to 2 ml with distilled water and incubated at 70° C for 1 hour. The reaction was stopped by adding 4 mls of 0.5 M perchloric acid and the fructose was determined by the cysteine - carbazole method (Dische Z & Borenfreund E., J. Biol. Chemi, 192,583 (1951)).

Activity levels of at least 64 units per ml of culture have been observed under standard assay conditions.

The amount of enzyme necessary to produce 1 mg of fructose from glucose per hr at 70° C under the above assay conditions was defined as one unit of enzyme.

Using the process of the invention it is possible to obtain good yields of enzyme both based upon the amount of carbon source used and upon the volume of the fermenter. Also the enzyme produced exhibits a high degree of activity in converting glucose to fructose.

The invention is illustrated by the following Examples:

EXAMPLE 1

Arthrobacter nov. sp strain NRRL B-3728 was grown continuously under conditions of carbon and nitrogen-limitation alternatively, in culture media containing two alternative carbon sources; glucose and xylose. The levels of glucose isomerase produced by the culture were assessed and related to cultural conditions.

The Medium used was as follows:
1.596 gms/l PO$_4$$^{3-}$
2 ml 40% Mg SO$_4$/liter
0.075 g/l Na$_2$ SO$_4$
0.45 g/l K$_2$ SO$_4$
0.05 g/l yeast extract
Trace elements (all ppm): Fe$^{2+}$ —3; Cu$^{2+}$ —0.075; Mn$^{2+}$ —0.375; Zn$^{2+}$ —0.345; Ca$^{2+}$ —0.075; H$_3$BO$_3$ —0.384; Na$_2$ MoO$_4$ —0.135

In experiments using nitrogen limitation, this medium was supplemented with 2.5 g/l (NH$_4$)SO$_4$. In carbon-limited experiments the pH was controlled using ammonia gas which also acted as a nitrogen source.

The carbon source was supplied as a 40% w/v solution of glucose or xylose and was pumped into the fermenter separately from the mineral salts medium to give a final concentration of 20 g/l carbohydrate.

Fermentation conditions a. A 5 liter fermenter was used in all cases with a working volume of approx. 2 liters.

b. Stirrer speed 1500 rpm.

c. pH was controlled at pH 6.9 by the automatic addition of ammonia gas, when under conditions of carbon limitation, and of alkali (4N NaOH, 4N KOH) when under conditions of nitrogen limitation.

d. Temperature was automatically controlled at 30° C.

e. Dissolved oxygen tension was continuously measured, recorded and controlled manually so as to be within the range 50-150 mm of mercury partial pressure.

f. Antifoam. Foam was controlled on an automatic programmed basis. The rate of antifoam addition varied with the cultural conditions employed.

g. The dilution rate was 0.11.

Enzyme Assays: These were performed by the assay method described above.

Protein determinations are expressed as total nitrogen × 6.25.

Sampling: A 250 ml sample of culture was taken, the cells were centrifuged and washed and then freeze-dried. Assays were performed on the freeze-dried sample. The samples were taken from the collection vessel which was cooled in a freezing mixture. This is preferable to taking samples directly from the fermenter since it does not involve removal of a large sample from the fermenter.

Inoculation: An inoculum which has been sub-cultured only 8 hrs. before inoculation was used.

A summary of the carbon conversions and enzyme yields obtained in the various fermentations is given in Table 1. It can be seen from Table 1 that there was no appreciable difference in enzyme yield, expressed as units/gm dry weight, when the substrate was altered.

TABLE 1

| Carbon Source | Limitation | Carbon Conversion (%) | Enzyme Yield (units/gm dry wt) |
|---|---|---|---|
| xylose | Carbon | 34 | 1150 |
| xylose | Nitrogen | 30 | 350 |
| glucose | Carbon | 46 | 1150 |
| glucose | Nitrogen | 31 | 350 |

A comparative batch culture experiment was performed using glucose as the carbon source. In this experiment the nutrient medium used was the same as that for continuous culture with an initial glucose concentration of 20.0 gms/l pH was controlled at 6.9 to 7.0 using ammonia gas.

Fermentation Conditions a. The fermenter used has a working volume of 5l.

b. Stirrer speed 750 rpm.

c. pH was controlled at 6.9 to 7.0 by automatic addition of ammonia gas.

d. Temperature was automatically controlled at 30° C.

e. The dissolved oxygen tension was measured and recorded but not controlled.

f. Antifoam. Foam was controlled by manual addition of antifoam as required.

g. The fermentation time was 30-35 hrs.

h. The inoculum was 1% by volume of a shaken-flask culture.

Enzyme assays and protein determinations were performed as described for continuous culture.

The results were as follows:
Carbon conversion 35%
Enzyme yield (units/gm dry wt) 730

EXAMPLE 2

Example 1 was repeated using Mycobacterium smegmatis strain ATCC 19420 with zylose as the carbon source. In this example however there were the following minor differences in the experimental conditions:

1. The temperature was automatically controlled at 37° C.

2. Samples were taken directly from the fermenter. The sampling method of Example 1 was not used due to the inhomogenous nature of the Mycobacterium Smegmatis culture.

The results are set out in Table 2. All figures are the average of at least 4 steady state determinations.

TABLE 2

| Carbon Source | Limitation | Enzyme Yield (units/gm dry wt) | Carbon Conversion % |
|---|---|---|---|
| xylose | Carbon | 350 | 40 |
| xylose | Nitrogen | 95 | 35 |

I claim:

1. A process for producing glucose isomerase enzyme by continuously cultivating a glucose isomerase-producing microorganism in a culture medium comprising a source of assimilable carbon and inorganic nutrients under conditions suitable for production of said enzyme and continuously recovering said enzyme wherein the concentration of a nutrient source in the culture medium is maintained at a level such as to be limiting to growth.

2. A process according to claim 1 wherein the nutrient source, whose concentration in the culture medium is maintained at a level which is limiting to growth, is the carbon source.

3. A process according to claim 1 wherein sources of carbon, nitrogen, phosphorus, magnesium, sulphur, potassium and organic nitrogen are added to the culture medium in concentrations (% w/w of the source compound) within the ranges:

Carbon source — 0.05 to 10%
Nitrogen source — 0.001 to 3%
Phosphorus source — 0.01 to 0.5%
Magnesium source — 0.001 to 0.2%
Sulphur source — 0.01 to 0.25%
Potassium source — 0.01 to 0.25%
Organic nitrogen source — 0.01 to 5%

4. A process according to claim 1 wherein the microorganism is a strain of a genus selected from the group consisting of Streptomyces, Arthrobacter, Mycobacterium and Curtobacterium.

5. A process according to claim 1 wherein the carbon source is selected from the group consisting of glucose and xylose.

6. A process according to claim 1 wherein the culture medium is maintained at a temperature within the range 20° to 55° C.

7. A process according to claim 1 wherein the pH of the culture medium is maintained within the range 6.0 to 8.0.

8. A process according to claim 1 wherein the dissolved oxygen tension (DOT) within the culture medium is controlled within the range 0 to 150 mms of mercury.

9. A process according to claim 8 wherein the dissolved oxygen tension (DOT) is controlled within the range 30 to 100 mms of mercury.

10. A process according to claim 1 wherein the dilution rate is within the range 0.05 to 0.4 $hrs^{-1}$.

11. A process which comprises isomerizing glucose to fructose wherein there is added in said isomerizing a glucose isomerase enzyme which has been produced by continuously cultivating a glucose isomerase-producing microorganism in a culture medium comprising a source of assimilable carbon and inorganic nutrients under conditions suitable for production of said enzyme and continuously recovering said enzyme wherein the concentration of a nutrient source in the culture medium is maintained at a level such as to be limiting to growth.

12. A process according to claim 11, wherein, during the production of the enzyme, the nutrient source, whose concentration in the culture medium is maintained at a level which is limiting to growth, is the carbon source.

13. A process according to claim 11 wherein during the isomerization the temperature is maintained within the range 20° to 90° C.

14. A process according to claim 11 wherein the pH of the glucose-containing liquor undergoing isomerization is maintained within the range 5 to 9.

15. A process according to claim 11 wherein ions selected from the group consisting of magnesium, cobalt and manganese ions are present during the isomerization.

* * * * *